(12) United States Patent
Howey

(10) Patent No.: US 8,042,536 B1
(45) Date of Patent: Oct. 25, 2011

(54) NEBULIZER APPARATUS

(75) Inventor: Shane Howey, Mission Viejo, CA (US)

(73) Assignee: Care 2 Medical, Costa Mesa, CA (US)

( * ) Notice: Subject to any disclaimer, the term of this patent is extended or adjusted under 35 U.S.C. 154(b) by 776 days.

(21) Appl. No.: 11/550,778

(22) Filed: Oct. 18, 2006

(51) Int. Cl.
*A61M 16/00* (2006.01)
*A61M 15/00* (2006.01)
*A61M 11/00* (2006.01)

(52) U.S. Cl. ......... 128/203.15; 128/200.14; 128/200.24; 128/203.12

(58) Field of Classification Search ................................
128/200.11–200.13, 200.15–200.2, 200.24,
128/203.25–203.27, 204.18, 204.212, 200.14,
128/200.21, 203.15–203.17, 204.21, 204.11,
128/203.12; 285/261
See application file for complete search history.

(56) References Cited

U.S. PATENT DOCUMENTS

| | | | | |
|---|---|---|---|---|
| 36,691 A * | 8/1863 | Ward | ............................ | 285/261 |
| 68,112 A * | 8/1867 | Rhodes | ........................ | 285/261 |
| 100,726 A * | 3/1870 | Coar | ............................ | 285/261 |
| 1,949,055 A * | 2/1934 | Lambie | ............................ | 285/5 |
| 3,746,000 A * | 7/1973 | Edwards | .................. | 128/200.16 |
| 3,842,833 A * | 10/1974 | Ogle | ........................ | 128/200.18 |
| 4,094,317 A * | 6/1978 | Wasnich | .................. | 128/200.16 |
| 5,277,175 A * | 1/1994 | Riggs et al. | .............. | 128/200.21 |
| 5,355,872 A * | 10/1994 | Riggs et al. | .............. | 128/200.21 |
| 5,546,930 A * | 8/1996 | Wikefeldt | ............... | 128/201.13 |
| 5,685,298 A * | 11/1997 | Idris | ........................ | 128/206.12 |
| 5,762,063 A * | 6/1998 | Coates et al. | ............. | 128/205.13 |
| 5,823,184 A * | 10/1998 | Gross | ....................... | 128/204.18 |
| 5,996,579 A * | 12/1999 | Coates et al. | ............. | 128/205.13 |
| 6,412,481 B1 * | 7/2002 | Bienvenu et al. | ......... | 128/200.21 |
| 7,600,511 B2 * | 10/2009 | Power et al. | ............. | 128/200.24 |
| 2002/0020409 A1 * | 2/2002 | Kidwell et al. | .......... | 128/200.14 |
| 2005/0247313 A1 * | 11/2005 | Niles et al. | ............... | 128/203.16 |

* cited by examiner

*Primary Examiner* — Justine Yu
*Assistant Examiner* — Annette Dixon
(74) *Attorney, Agent, or Firm* — Venable LLP; Stefan J. Kirchanski

(57) ABSTRACT

A nebulizer apparatus for delivering medication in the form of an aerosol to a patient. The apparatus includes a medication reservoir for receiving liquid medication, a face mask for delivering aerosol to a patient, an attachment to a nebulizer machine or Bag resuscitator to generate carrier gas flow, a face mask or tubing to deliver the aerosol to the patient, and hosing to inter-connect the nebulizer components. The medication reservoir of the nebulizer apparatus includes rapid injection ports for the addition of medication to the medication reservoir, and is connected to the face mask via a dual sided ball and socket connection.

1 Claim, 7 Drawing Sheets

NEBULIZER APPARATUS

BACKGROUND OF THE INVENTION

1. Area of the Art

This invention relates generally to devices used in respiratory therapy, and more particularly, to an improved apparatus for delivering a continuous dosage of aerosol medication to a patient.

2. Description of the Prior Art

Nebulizers are well known in the art, and are designed to deliver an aerosol of medication to the respiratory tract of a patient. A nebulizer apparatus is composed of a medication reservoir, a face attachment, and hosing to connect the components of the nebulizer to a carrier gas source, such as an oxygen tank, a respirator, resuscitator bag, or other pump. During operation, the nebulizer creates a flow of oxygen that intermixes with the liquid medication held in the medication reservoir. The intermixing of medication and oxygen forms an aerosol of oxygen and the medication, which is delivered to the lungs of the patient through a face attachment, such as a face mask.

Nebulizers have been utilized for treating various respiratory ailments ranging from common colds to severe asthma and complex infections of the bronchial system. Certain respiratory ailments can be more effectively treated by the delivery of medication to the patient as an aerosol, as opposed to taking the medication orally or through intra-venous administration. The uses of nebulizer apparatus are not limited to respiratory ailments; they may also be used in the treatment of coronary sclerosis, coronary thrombosis and other ailments. An advantage of using a nebulizer apparatus to treat these ailments is that medicated aerosol may be carried deep into the patient's lungs. In addition, the air transmitted to the patient through the nebulizer may be humidified, or heated.

Moreover, the treatment of medical conditions using nebulizers is not limited to hospitals or other treatment centers. In addition to stationary devices, devices to heavy or bulky to be transported, nebulizers may also take the form of portable devices. Paramedic emergency medical technicians ("EMT-P") frequently use nebulizers to administer albuterol and other medications in the field, or in transit, during an emergency medical response.

There are, however, problems that interfere with the efficacy of nebulizer systems currently known in the art. These problems are particularly acute in the context of emergency medical situations in which patients are treated in the field or in transit to a hospital or other treatment center. One such problem with existing nebulizer systems, is the need to disassemble the nebulizer in order to add a medication dose to the nebulizer's medication reservoir. While in the field, or in transit, the disassembly of the nebulizer apparatus requires an EMT-P or other emergency responder to divert their attention from the emergency medical situation. The disassembly of the nebulizer apparatus to add medication may also take time that may be critical for other required emergency treatment of the patient.

Another problem with existing nebulizer systems is that spillage of medication from the medication reservoir frequently occurs during field treatment of a patient or during the transport of a patient to a treatment center. Patients often must be treated in a variety of positions, such as on their backs, sides, stomachs, or sitting upright. Many prior art medication reservoirs are not adapted to be variably positioned, and spillage of medication from the reservoir will occur unless the device (and the patient) are maintained in an upright position. Moreover, treatment often occurs in transit to a treatment center, where the patient is subject to various vibrations and motion associated with automobile travel. This vibration and motion makes it difficult to disassemble the medication reservoir and add medication without causing spillage.

Therefore, it is an object the present invention to provide an improved nebulizer apparatus for the delivery of aerosolized medication to a patient. The apparatus incorporates a medication reservoir that may be variably positioned to prevent medication spillage. The improved apparatus also incorporates a rapid medication injection port for the introduction of medication to the medication reservoir without having to disassemble the nebulizer apparatus.

SUMMARY OF THE INVENTION

The present invention is directed to an improved nebulizer apparatus for delivering medication in the form of an aerosol to a patient. The apparatus includes a medication reservoir for receiving liquid medication, an attachment to a nebulizer or Bag resuscitator to generate carrier gas flow, a face mask or tubing to deliver the aerosol to the patient, and hosing to inter-connect the nebulizer components.

During operation, the carrier gas flow travels through the hosing to the medication reservoir. The carrier gas intermixes with the liquid medication held in the medication reservoir to form an aerosol. This aerosol is mixed with additional gas (as from a resuscitator bag) and then flows through the hosing to the face mask or tubing to be delivered to the respiratory tract of the patient.

The medication reservoir of the improved nebulizer apparatus is connected to the nebulizer apparatus through a dual sided hollow ball and socket joint. This hollow ball and socket joint allows the medication reservoir to be positioned in a substantially vertical manner independent of the motions or position of the patient. The medication reservoir of the improved nebulizer apparatus also features a rapid medication injection port for the delivery of medication to the medication reservoir without the need to disassemble any portion of the nebulizer apparatus.

In one embodiment of the present invention, the medication reservoir is connected directly to a mask that is positionable over the nose and mouth of a patient. In an alternate embodiment of the present invention, the medication reservoir is connected to a resuscitator bag, or other gas source, and a flexible tube connected to an apparatus for intubation of a patient. As in the previous embodiment, the connection between the medication reservoir and the other components of the nebulizer apparatus is via a dual sided ball and socket connection. The medication reservoir may also contain the rapid medication injection port.

DESCRIPTION OF THE FIGURES

The present invention will be more fully understood when the specification herein is considered in conjunction with the drawings, wherein.

DETAILED DESCRIPTION OF THE INVENTION

Figure 1:
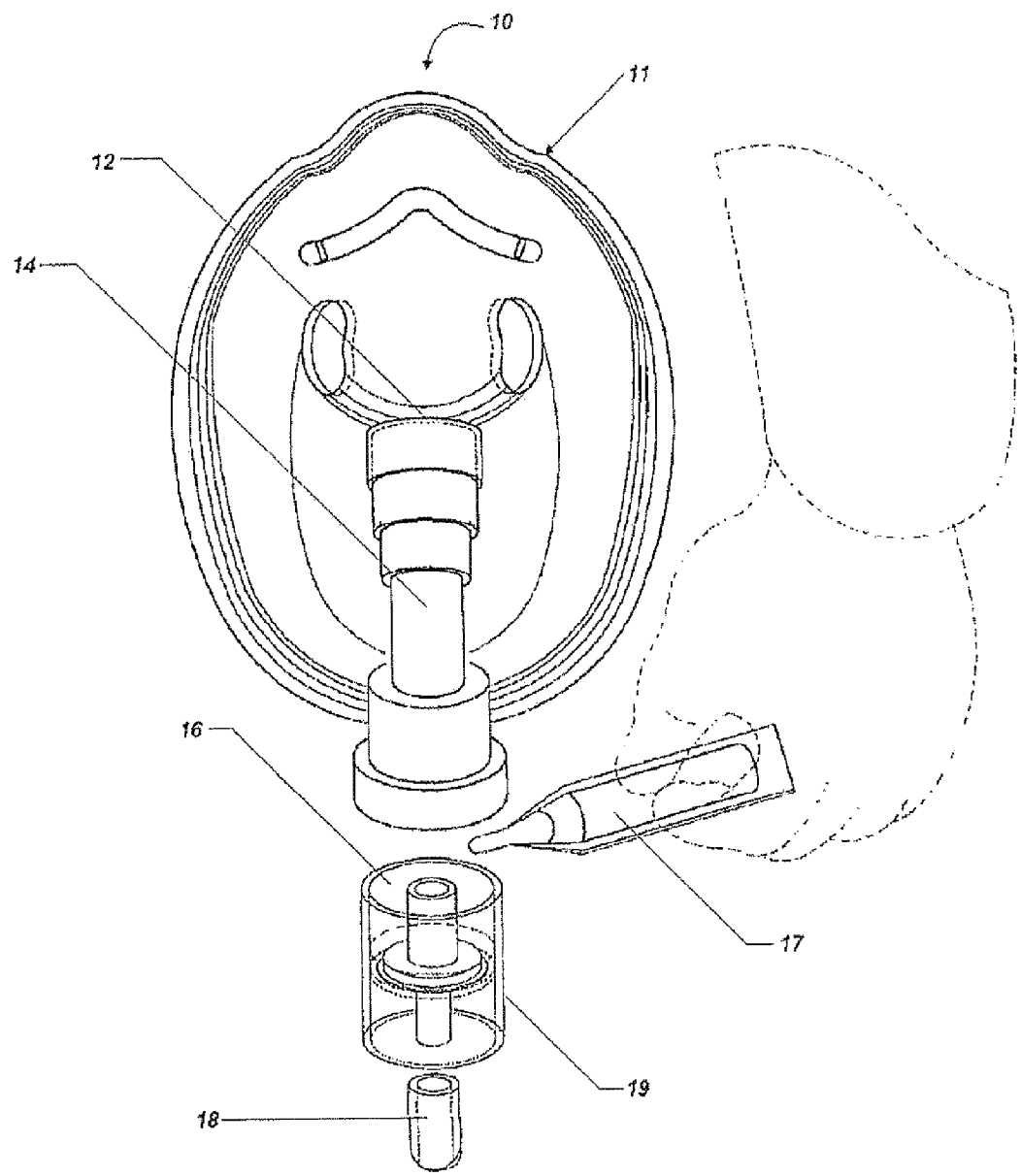
FIG. 1 is a front view of a prior art nebulizer apparatus, having a face mask and a medication reservoir. The illustration includes a representation of how the medication reservoir is filled.
Figure 2:
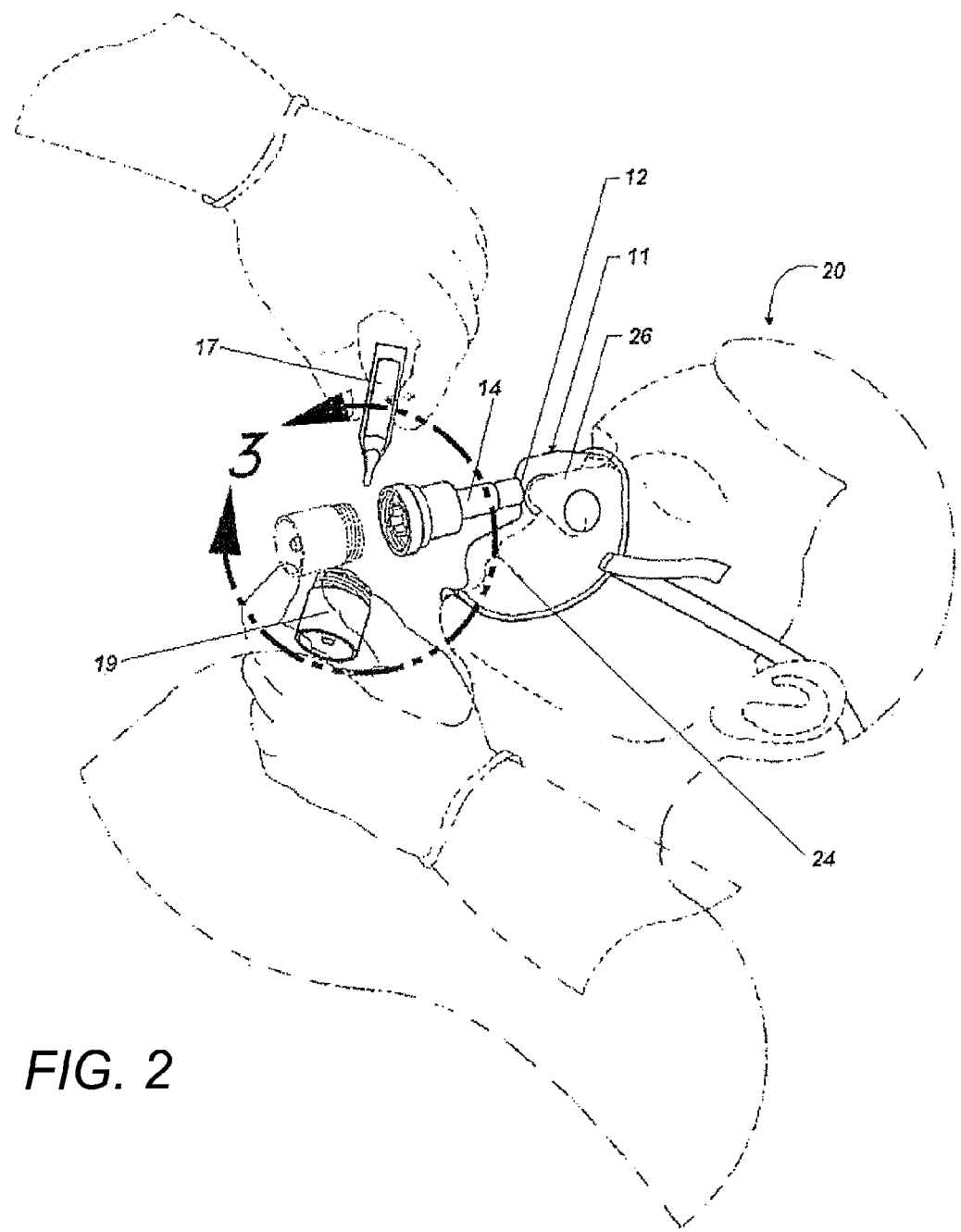
FIG. 2 is a side view of a prior art nebulizer apparatus being used for a patient lying on their back or at an angle.
Figure 3:
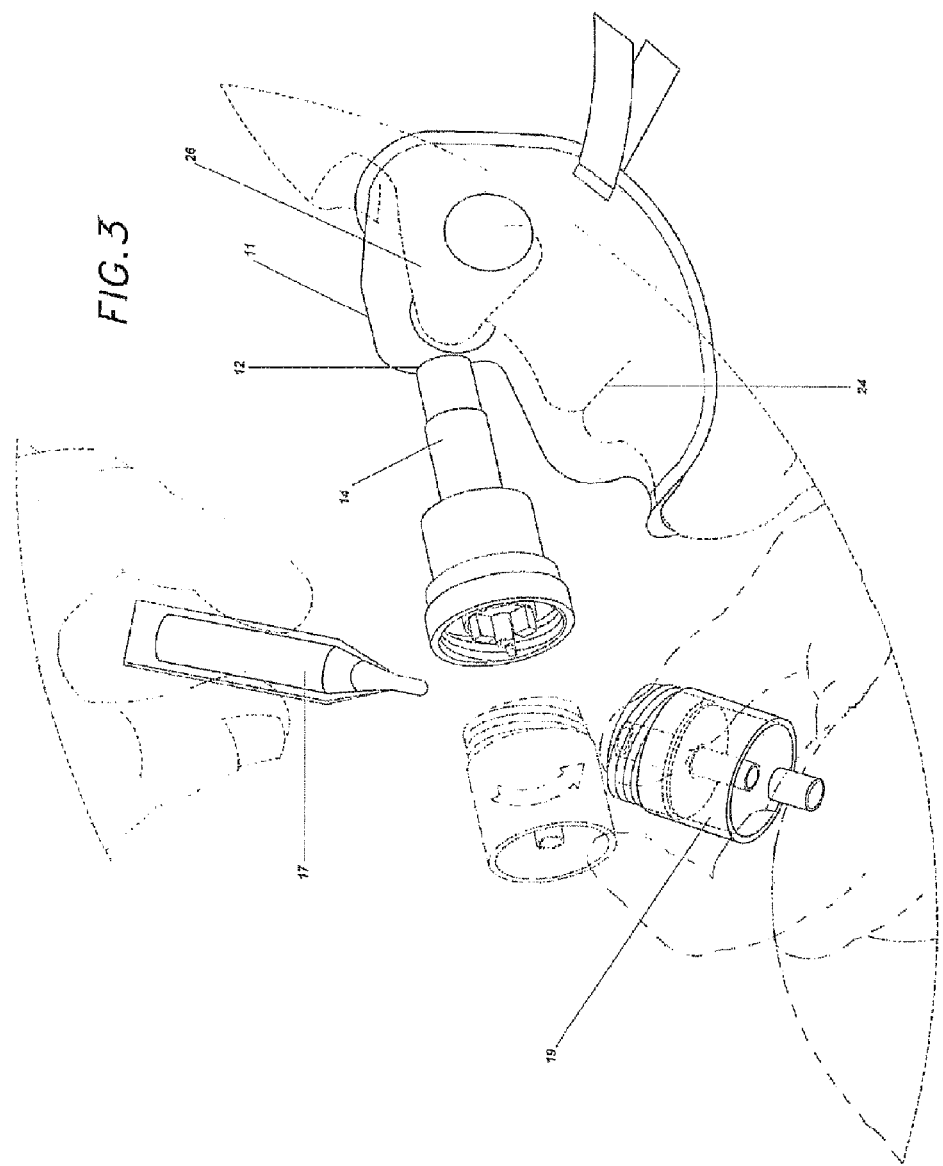
FIG. 3 is a magnified view of a prior art nebulizer apparatus being used for a patient lying on their back or at an angle.
Figure 4:
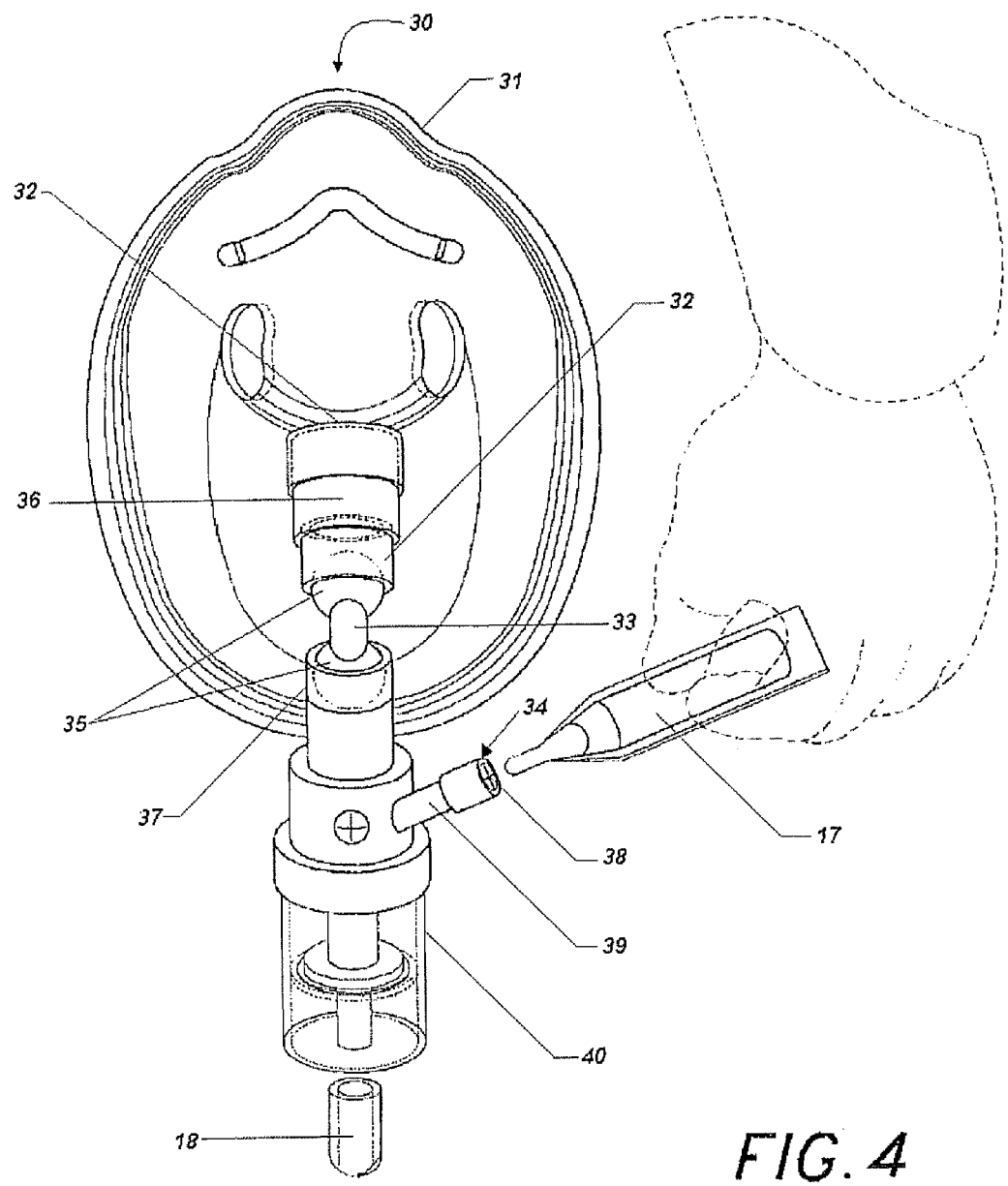
FIG. 4 is a front view of one embodiment of the nebulizer apparatus contemplated by the current invention, including: a face mask, a medication reservoir, a hollow ball and socket joint connecting the face mask to the medication reservoir, and a rapid injection port.
Figure 5:
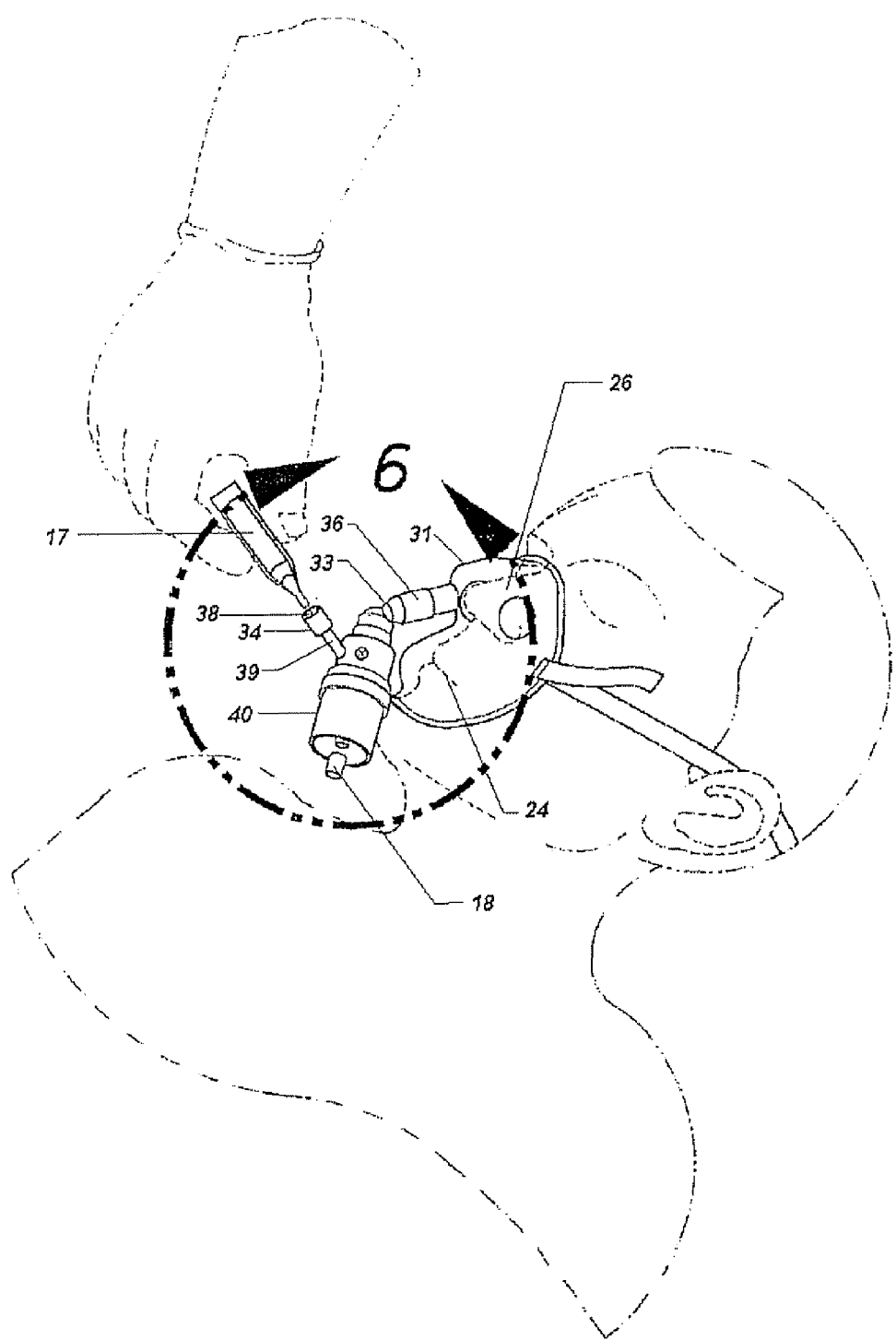
FIG. 5 is a side view of an embodiment of the nebulizer apparatus as contemplated by the current invention being used for a patient lying on their back or at an angle.
Figure 6:
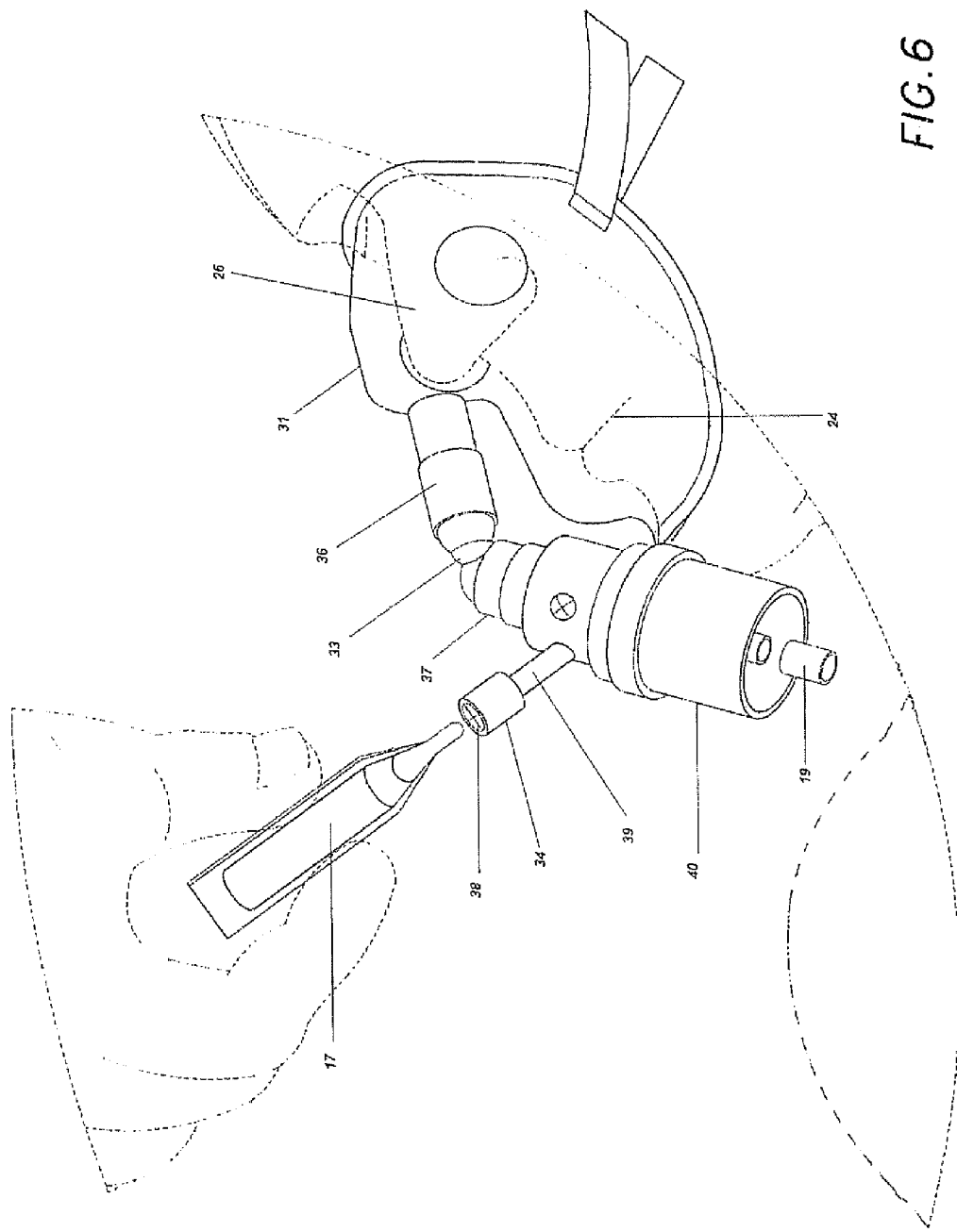
FIG. 6 is a magnified side view of one embodiment of the nebulizer apparatus as contemplated by the current invention being used for a patient lying on their back or at an angle.
Figure 7:
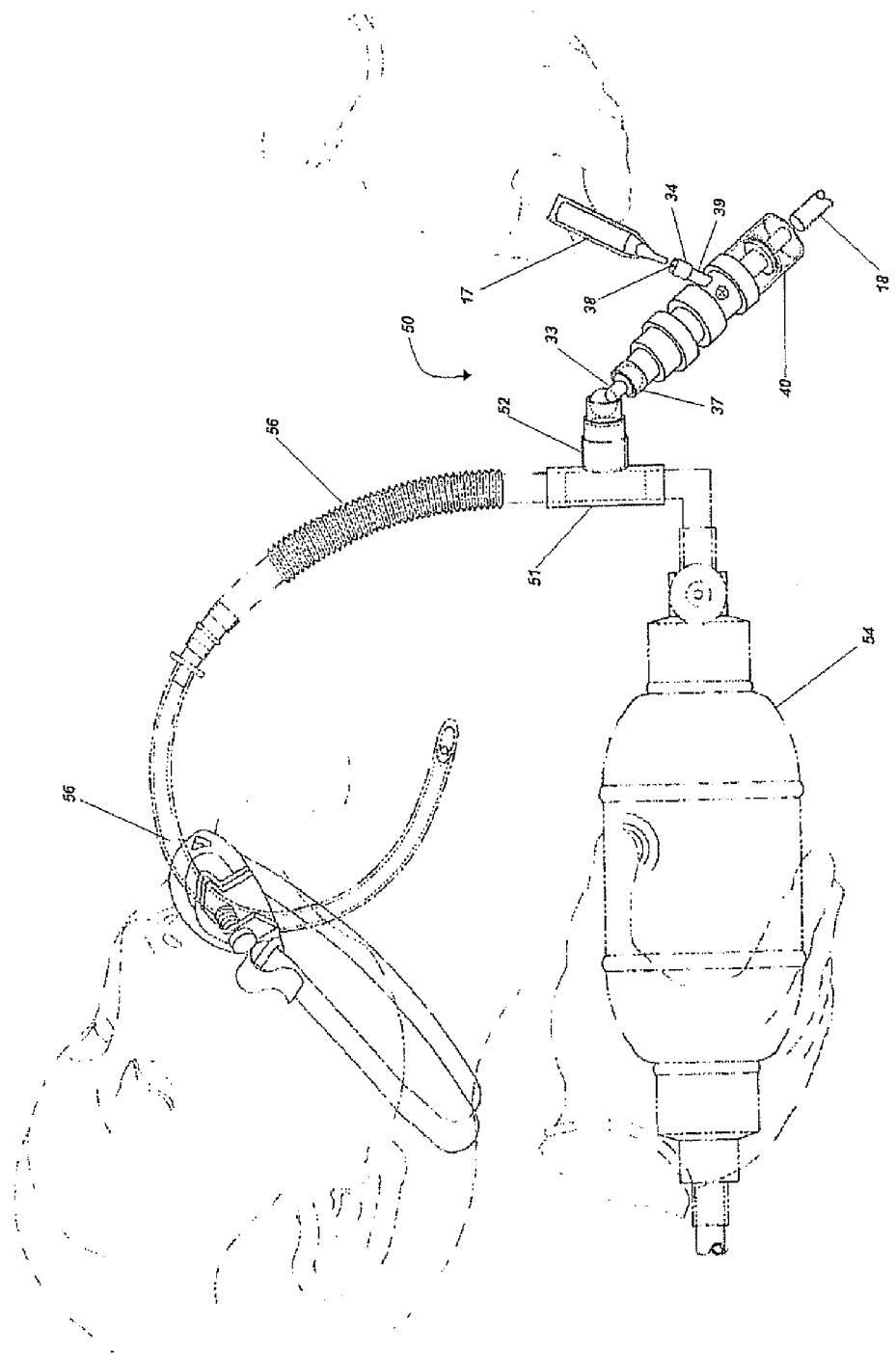
FIG. 7 is a side view of an alternate embodiment of the nebulizer apparatus of the current invention, including: a resuscitator bag, hosing, medication reservoir, hollow ball and socket joint, rapid injection port, and intubation tube.

The following description is provided to enable any person skilled in the art to make and use the invention and sets forth the best modes contemplated by the inventor of carrying out his invention. Referring to FIG. 1, a prior art nebulizer apparatus 10 is represented. The apparatus is composed of a face mask 11, medication reservoir 40 and hosing 18 from the carrier gas source. The liquid medication in the medication reservoir 40 is aerosolized by the flow of carrier gas (usually oxygen) through the medication reservoir 40. The resulting aerosol flows through a hollow plastic housing 14 connecting the medication reservoir 40 to the face mask 11 of the nebulizer apparatus 10, and out of an outlet 12 for delivery to the patient.

In order to add medication to the medication reservoir of the prior art nebulizer apparatus 10, the medication reservoir 40 must be disconnected from the plastic housing 14, and the gas source must be shut down. Once the medication reservoir is disconnected, medication may be added to the opening of the medication reservoir 16 through a standard needle and syringe, needleless syringe, or other dispenser 17. During the disconnection of the medication reservoir, the ventilation circuit from the respirator, bag resuscitator or nebulizer to the patient is necessarily interrupted with possible harm to the patient.

The method of adding medication to the medication reservoir of a prior art nebulizer apparatus has a number of highly undesirable aspects. A patient requiring ventilation and treatment via an aerosol medication, as in the case of a severe asthma attack, is gravely ill. The interruption of oxygen delivery to a patient during an emergency, or other serious condition, can be life threatening. Moreover, the disconnection of the medication reservoir during an emergency response or other treatment can result in spillage of the liquid medication, and increased risk of contamination and infection.

In addition to the problems associated with disconnecting the medication reservoir from the nebulizer apparatus, a prior art nebulizer apparatus also fails to accommodate the variety of positions a patient may be treated in. This deficiency can become particularly problematic in the context of an emergency medical response. For instance, a prior art nebulizer apparatus requires that the medication reservoir of the apparatus be in a substantially upright position. FIGS. 2 and 3 illustrate the use of a prior art nebulizer apparatus 10 with a patient 20 lying on their back. The orientation of the patient prevents the medication reservoir 19 from being oriented vertically. The improper orientation of the medication reservoir 19 prevents the liquid medication within the medication reservoir 19 from being properly aerosolized and delivered to the patient 20, and the liquid medication may also spill into the face mask 11 of the apparatus 10, and, possibly, into the nose 26 and mouth 24 of the patient. Moreover, the addition of liquid medication using a syringe 17, or other suitable device, is difficult because the nebulizer apparatus must be disassembled to access the medication reservoir 19. In addition, the need to shut off the source of carrier gas is a further inconvenience.

FIG. 4 illustrates a preferred embodiment of the inventive nebulizer apparatus. The nebulizer apparatus 30 includes a face mask 31 designed to enclose the nose and mouth of the patient. In a preferred embodiment, the face mask 31 is constructed of a flexible material, such as a flexible plastic, to fit comfortably on the face of the patient. The face mask may also include a compressible plastic bladder, or other pad, running along the edge of the portion of the mask that receives the patient's face, ensuring a snug and comfortable fit. In one preferred embodiment all of these components or at least those that contact the patient are designed for single use and are disposed of following that use.

The face mask 31 of the inventive nebulizer apparatus 30 is connected to a medication reservoir 40 through a housing 36, and a hollow member 33 having two, substantially spherical ends 35. The housing 36 is substantially tubular, with one end coupled to the face mask 31, and the other end 32 constructed to receive a spherical end of the hollow member 33. The spherical end of the hollow member 33 fits into the end 32 of the housing 36, resulting in a ball and socket connection between the housing 36 and the hollow member 33. Likewise, the other spherical end of the hollow member 33 fits into a receiving structure 37 of the medication reservoir 40, resulting in a ball and socket connection between the medication reservoir 40 and the hollow member 33.

The ball and socket connection between the hollow member 33 and both the housing 36 and the medication reservoir 40 allows a range of motion between the face mask 31 and the medication reservoir 40. In fact, the hollow member 33 may rotate with two degrees of freedom about its connection to either the housing 36 or the medication reservoir 40. As will be shown in FIGS. 5 and 6, the range of motion between the face mask 31 and medication reservoir 40 allows the nebulizer apparatus of the current invention 30 to effectively deliver aerosol medication to a patient in various positions, such as on their side, back, or stomach.

In an alternate embodiment of the current invention, the hollow member 33 may form a ball and socket connection directly with a receiving structure of the face mask 31. The direct connection of the hollow member 33 and the face mask 31 may simplify the manufacture of the inventive nebulizer apparatus, or improve its durability. In addition, the ball and socket connection between the hollow member 33 and the housing 36, face mask 31, or medication reservoir 40, may be disconnected, providing for easier storage and cleaning of the nebulizer apparatus 30 in situations where disposable apparatus is not used.

The medication reservoir 40, connected to the face mask 31 by the hollow member 33, is where liquid medication, such as albuterol, saline, or other medication, is intermixed with a carrier gas; such as oxygen or air, to create a medicated aerosol. The carrier gas is delivered to the inventive nebulizer apparatus 30 through tubing 18 connected to a gas source. The medicated aerosol flows from the medication reservoir 40 through the hollow member 33 and through the housing 36 to the face mask 31 of the nebulizer apparatus 30. Upon inhalation or exhalation of the patient, the medicated aerosol flowing to the face mask 31 is then delivered to the patient through their nose or mouth.

The liquid medication is introduced to the medication reservoir 40 through a rapid injection port 34. In one embodiment, the rapid injection port may be located on the side of the medication reservoir 40, and in a position towards the top of the medication reservoir 40, or near the receiving structure 37 of the ball and socket connection. It will be apparent that multiple injection ports can be supplied at different locations on the device—even on the ball and socket connector. Multiple injection ports permit additional doses of the initial medication or doses of a different medication to be in place for instantaneous injection when they are needed. The rapid injection port 34 includes a short inlet tube 39 extending outward from the outer surface of the medication reservoir 40. In the preferred embodiment, the short inlet tube 39 of the rapid injection port 34 is at a slight upward angle from the horizontal plane normal to the side wall of the medication reservoir 40.

One end of the short inlet tube 39 opens into the medication reservoir 40, with the other end terminating at a gate 38, composed, for example, of a flexible piece of plastic, fabric, or other material, for receiving a drug dispenser 17. In one embodiment, the gate 38 is composed a plurality of plastic sheets, defining a single plane, which fit snugly together along cuts radially placed from the center point of the gate. Upon placement of a dispenser 17 at the gate, the plurality of plastic sheets bend inward to receive the tip of the dispenser 17. Medication may then be delivered to the medication reservoir 40 through the gate 38 and through the short inlet tube 39.

The inventive nebulizer apparatus 30 may be fabricated from a flexible material such as plastic or rubber, or other materials. It may be desirable, however, for certain components, such as the housing 36, rapid injection port 34, hollow member 33, and medication reservoir 40, to be constructed of a strong, durable material, that need not be flexible, such as a stiff plastic, glass, or a polyester or epoxy resin. Moreover, it may be desirable that the materials comprising the face mask 31, housing 36, rapid injection port 34, hollow member 33, and medication reservoir 40 be transparent such that the medicated aerosol is visible in nebulizer apparatus 30.

The present invention provides an improved nebulizer apparatus with great advantages over the prior art. As shown in FIGS. 5 and 6., the ball and socket connections between the hollow member 33 and the housing 36, and medication reservoir 40 allow for the effective delivery of medicated aerosol to patients lying on their backs or in virtually any other position. The ball and socket connections ensure that the medication reservoir 40 is maintained in a substantially vertical orientation independent of the position of the patient. As a result, the liquid medication is properly aerosolized and delivered to the patient, and there is no spillage of the liquid medication.

An alternate embodiment of the nebulizer apparatus 50 for use with a resuscitator bag is depicted in FIG. 7. As in the previous embodiment the medication reservoir 40 contains a rapid injection port 34, and is connected to a conduit for carrier gas 18. A tubular member having two substantially spherical ends 33 couples to a receiving structure 37 on the top of the medication reservoir 40. The other spherical end of the tubular member 33 couples to a receiving structure 52 of a T-junction 51, or other tubular connector. The T-junction is further coupled to a resuscitator bag 54 and a flexible tube 58. The flexible tube may couple to a tube for intubation 56, such as an endotracheal tube, or a face mask.

While this detailed description represents the preferred embodiments of practicing and making the current invention, various modifications will remain readily apparent to those skilled in the art. As a result, the following claims are to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A nebulizer apparatus for use with a source of carrier gas flow for providing aerosolized medication to a patient, the nebulizer apparatus comprising:

a medication reservoir for containing liquid medication having a carrier gas input to deliver pressurized gas to form aerosolized medication from the liquid medication, a receiving structure through which the aerosolized medication exits the medication reservoir, and a rapid injection port for adding and replenishing medication to the medication reservoir without interrupting formation or delivery of the aerosol, a T-junction connector element having a receiving structure connected to a first opening thereof, and with a flexible tube for conducting aerosolized medication to a patient connected to a second opening thereof, wherein the receiving structure of the medication reservoir is coupled to the receiving structure of the T-junction connector element so that the connector element can deliver aerosolized medication to the flexible tube; and a resuscitator bag, having an output coupled to a third opening of the T-junction connector element.

* * * * *